United States Patent [19]

Bigeard et al.

[11] Patent Number: 5,770,154

[45] Date of Patent: Jun. 23, 1998

[54] DEVICE FOR TESTING AND FOR ANALYZING A PETROCHEMICAL PROCESS

[75] Inventors: Pierre Bigeard, Vienne; Stephane Kressmann, Serezin du Rhone; Christophe Gueret, Vienne; Pierre Galtier, Vienne; Julia Magne-Drisch, Vienne, all of France

[73] Assignee: Institut Francais du Petrole, France

[21] Appl. No.: 578,223

[22] Filed: Dec. 26, 1995

[30] Foreign Application Priority Data

Dec. 26, 1994 [FR] France ................................... 94 15741

[51] Int. Cl.$^6$ .............................................. G01N 35/00
[52] U.S. Cl. .......................... 422/80; 422/68.1; 422/109; 422/130; 436/34; 436/37
[58] Field of Search .............................. 422/80, 83, 198, 422/89, 109, 130, 68.1; 436/34, 37, 174, 181

[56] References Cited

U.S. PATENT DOCUMENTS

| | | | |
|---|---|---|---|
| 2,753,246 | 7/1956 | Shields et al. .............................. | 436/37 |
| 3,414,382 | 12/1968 | Kapff et al. ................................ | 436/37 |
| 4,120,663 | 10/1978 | Fally ........................................ | 422/198 |
| 4,281,119 | 7/1981 | Lagow et al. ............................ | 544/106 |
| 5,264,183 | 11/1993 | Ebner et al. .............................. | 436/34 |
| 5,266,270 | 11/1993 | Ajot et al. ................................. | 422/80 |

FOREIGN PATENT DOCUMENTS 2 583 519   12/1986   France .

OTHER PUBLICATIONS

ASTM Designation D 3907–86, Standard Method for Testing Fluid Cracking Catalyst by Microactivity.

Soviet Inventions Illustrated, Section Ch., Wk. 8726, Jul. 8, 1987, Derwent Publications, Ltd., London, GB SU–A–1 269 824, 15 Nov. 1986.

*Primary Examiner*—Hien Tran
*Attorney, Agent, or Firm*—Millen, White, Zelano & Branigan, P.C.

[57] ABSTRACT

A device for testing the development of processes or chemical reactions in the presence of solid catalysts comprising a reactor of cylindrical shape, of inside diameter D and of length L, such that 50<L/D<150. The reactor having a preferred D of 10–40 mm also includes a sheathed thermometer arranged substantially along the axis of the reactor.

16 Claims, 2 Drawing Sheets

DEVICE FOR TESTING AND FOR ANALYZING A PETROCHEMICAL PROCESS

SUMMARY OF THE INVENTION

The present invention relates to a device for testing the development of processes or chemical reactions in the presence of solid catalysts, notably in the divided form. The device of compact dimensions preferably comprises notably a reactor with optimized dimensions, for example reactor heating means, load preheating means, regulating means, heat insulation means that contribute to obtaining test results that proved to be reliable, industrially reproducible, and of simplified and therefore cheap implementation.

The invention can be used for multiple applications, notably:

in refining, for example:
  *hydrotreatings,
  *hydrocracking,
  *hydrogenations,
  *hydroisomerization,
  *reforming,
  *catalytic cracking,
in petrochemistry, for example:
  *conversion of aromatics (isomerization, disproportionation, hydrodealkylation),
  *various oxidations (oxidation of toluene into benzaldehyde, of methanol into formol),
in $CO+H_2$ chemistry (synthesis gas processing):
  *synthesis of methanol,
  *conversion of methanol into hydrocarbons,
  *conversion of $CO+H_2$ into higher alcohols.

The purpose of the device according to the invention is notably to obtain:

a pilot test equipment of compact dimensions allowing to obtain results representative of industrial plants,
  a substantially isothermal temperature regulation along the axis of the reactor,
  a good control of the temperature regularity in the radial direction of the reactor (isothermal temperature),
  the use of a small quantity of catalyst,
  a sufficiently efficient preheating of the load prior to its entry in the reactor,
  a flow regime of the fluids in the reactor substantially of the "piston" type, limiting "backmixing" phenomena,
  appropriate gas and liquid velocities of the fluids in order to allow results representative of industrial plants to be obtained,
  limited heat losses, especially between the preheat furnace and the reactor,
  an appropriate system for keeping the temperature of the reactor, allowing to avoid local overheatings and radial and axial heat losses with respect to the reactor.

In order to reach these objectives, the present invention relates to a device for testing and for analyzing a chemical reaction using a load placed in contact with at least one catalyst, the device comprising at least one reactor containing the catalyst, means for heating the reactor, means for controlling the temperature of the reactor, means for preheating the load prior to its entry in the reactor, heat insulation means. The reactor has a cylindrical shape of inside diameter D and of length L, such that $50<L/D<150$. The temperature control means include at least one sheathed thermometer arranged substantially along the axis of the reactor and the reactor, arranged substantially vertically, receives the load through its lower or upper end.

The preheating means can comprise a coil-shaped load delivery line and means for heating said coil.

The heat insulation means can insulate both the reactor and the load delivery line.

The coil can be a double-wall pipe, the outer wall being made of a metal of good heat conductivity, copper for example.

The sheathed thermometer can have a diameter ranging between 3 and 6 mm and it can comprise thermocouples distributed over the whole of its length.

The value $L/D$ can range between 70 and 100.

D can range between 10 and 40 mm.

The reactor can have a diameter D of about 16 mm and a length of about 1500 mm.

The heat insulation means can consist of a cylindrical jacket made of two half shells placed around the means for heating the reactor and the means for preheating the load delivery coil.

The means for heating the reactor can consist of a series of electric resistors embedded in metallic half rings surrounding the reactor, said half rings being welded to each other so as to form two half shells around the reactor, and each ring consisting of two half rings can comprise at least one means for measuring its temperature and each of the thermocouples of the sheathed thermometer can be situated in the neighbourhood of the transverse plane comprising said means for measuring the temperature of each ring.

The control means can comprise means for regulating the electric supply of each ring according to the temperature measured by the thermocouples of the sheathed thermometer and possibly by the means for measuring the temperature of each ring.

BRIEF DESCRIPTION OF THE DRAWINGS

Other features and advantages of the invention will be clear from reading the description hereafter, followed by non limitative examples and tests, with reference to the accompanying drawings in which.

DESCRIPTION OF THE PREFERRED EMBODIMENTS

Figure 1:
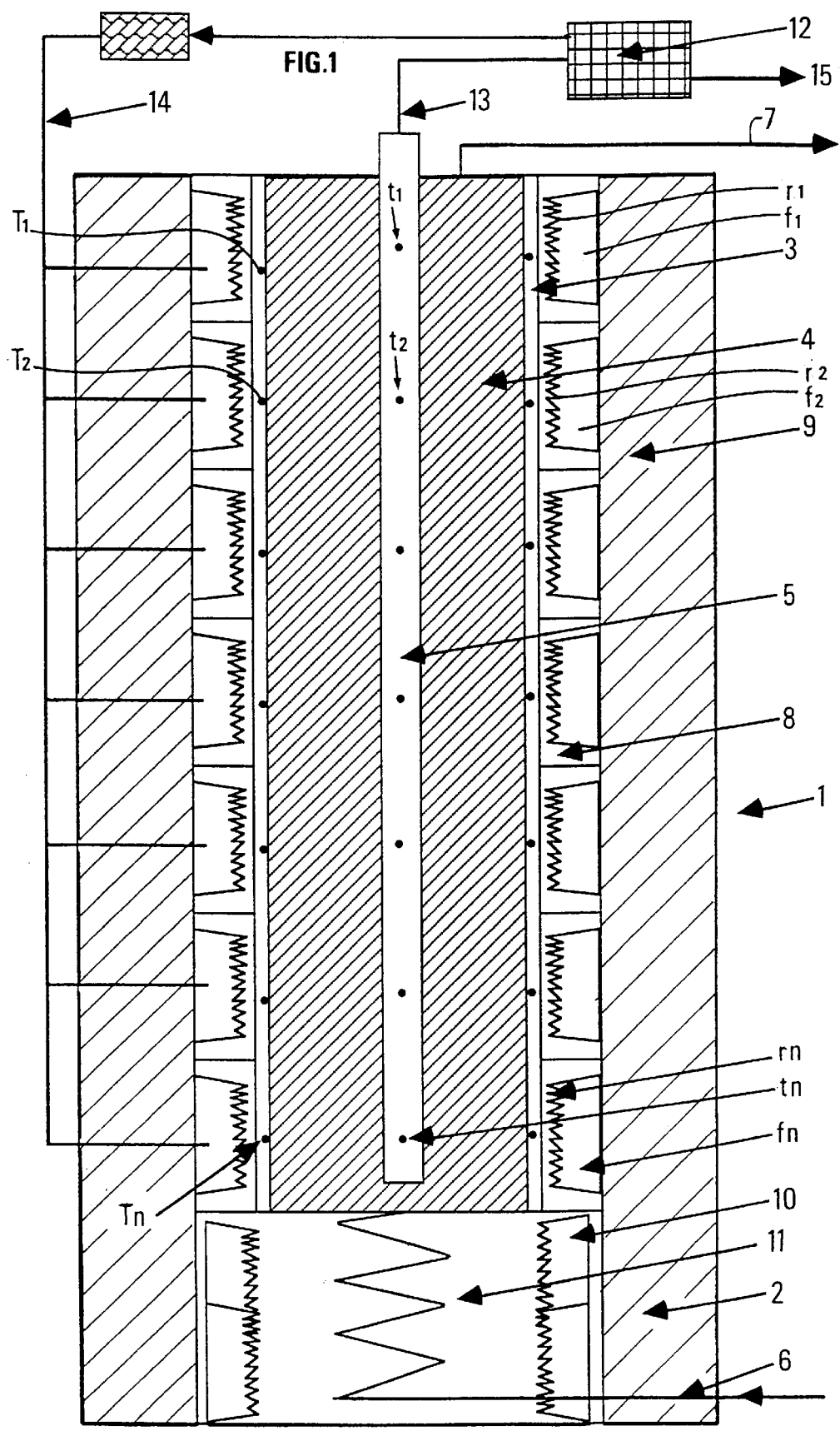
FIG. 1 diagrammatically shows a preferred embodiment of the device according to the invention.

In FIG. 1, reference numbers 1 and 2 respectively show the two main zones of the device: the chamber containing the reaction zone and the zone for preheating the load prior to its entry in the reactor.

Reactor 3 proper consists of at least one tube, preferably cylindrical, of inside diameter D and of length L. The catalyst is placed in at least one annular space 4 defined by the inner space of the reactor (or tube) and the outside of a sheathed thermometer 5 arranged substantially along the axis of the tube and extending preferably at least over the whole length L. The sheathed thermometer preferably includes a series of thermocouples $t1, t2, \ldots, tn$ distributed substantially regularly over the whole length of the thermometer. Pipes 6 and 7, respectively intended for the injection of the load and for the discharge of the conversion product or products, are connected by suitable means to the two ends of the reactor. The reactor is preferably arranged vertically and injection pipe 6 is then connected to the base of the reactor.

Furnace 8 (heating means) generally consists of a pile of rings $f1, f2, \ldots, fn$ around and in close contact with the reactor tube. These rings are welded two by two so as to form two monobloc half shells articulated in relation to each other. These half shells can thus open to allow the reactor to be mounted and close when the plant is operated. This new design of the heating means allows to ensure a limited waste of the heat diffused along a radial or an axial direction in relation to the reactor. These rings comprise electric heating resistors r1, r2, . . . , rn embedded in the mass of the half rings and so arranged that they are situated in direct proximity to the outer surface of the reactor. Furthermore, each ring is provided with at least one temperature measuring means T1, T2, . . . , Tn. The thermocouples of the measuring means are situated as close as possible to the reactor, preferably in contact with the surface of the reactor and held in this position by springs.

The purpose of the load preheating zone 2 (preferably electric preheating means) is to control the temperature conditions of the load when it enters the reactor and moistens the catalyst. For an optimum evolution of certain reactions, in the case of exothermic reactions, furnace 2 is used to control precisely the inlet temperature of the load when it enters the reactor and consequently to control the reaction temperature in the reactor efficiently. For example, for a hydrotreating reaction temperature of about 380° C., the distillate can be preheated to 300° C. In this case, it is desirable to have no or little heat losses between the preheating means and the reactor heating means. To that effect, the device preferably comprises two cylindrical half shells 9 made of a thermal insulation material that surround both the reactor heating means or rings 1, f1, f2, . . . , fn and the preheating zone 2. The preheating means preferably consist of a coil-shaped pipe 11 through which the load circulates. The coil runs on from injection pipe 6 and from the electric heating means, for example resistors 10. In this first variant, the coil surrounds the electric resistor. The assembly consisting of the coil and of the electric resistor is embedded in a heat-conducting material. The electric resistor transmits in this case the thermal energy to the load by conduction.

It is also preferable to have no or little thermal cracking during the load preheating phase, that could in fact cause errors in the catalyst performances and also lead to a coking in the furnace coil that would get clogged up after a while. To that effect, one can attempt to overcome these thermal cracking phenomena in the coil. One solution can consist in a slow preheating of the load, which is sometimes incompatible with the search for a small-size device. The present device can use a double-wall coil. The conventional tube, generally made of stainless steel, is surrounded by a copper tube that is drawn on the conventional tube before the assembly is given the shape of a coil.

The heat regulation means include control means 12 schematically connected by lines 13 and 14 to the temperature measuring means t1, t2, . . . , tn and T1, T2, . . . , Tn. The heat regulation is designed to obtain a substantially isothermal regulation along the axis of the reactor, whether the reactions are endothermic or exothermic. The measurements provided by the thermocouples t1, t2, . . . tn are processed and interpreted by control means 12, which act accordingly by sending supply commands (symbolized by the arrow bearing reference number 15) or cutoff commands to certain electrodes of rings f1, f2, . . . , fn. The measurements provided by thermocouples T1, T2, . . . , Tn can have an effect on the regulation system, but they are preferably safety measures.

It has been determined that the dimensions of the reactor, inside diameter D and length L, have an optimum ratio L/D ranging between 50 and 150 and preferably between 70 and 100. The purpose of heat regulation is to obtain in the reactor an isothermal temperature as perfect as possible in the axial as well as in the radial direction. The purpose of this second condition is to limit the effect referred to as thermal "cupel", i.e. in the same transverse plane in relation to the axis of the reactor, the temperature close to the center (of the sheathed thermometer) is not identical to the temperature on the inner wall of the reactor. Considering the reduced size of the device (notably in order to limit the quantity of catalyst necessary, to decrease the thermal inertia and to facilitate the implementation of the catalytic reaction), dimensions D preferably ranging between 10 and 40 mm have been selected. It has been established that the reactor must have a sufficient slenderness ratio or height to be able to work under the best thermal conditions and to have a fluid flow regime very close to the "piston" type and sufficient gas and liquid linear velocities, which allows to obtain good result representative of industrial plants. The reactor tube preferably can have a length L=1500 mm and an inside diameter D=16 mm.

The following examples will show the efficiency of the device according to the invention:

EXAMPLE 1

The device according to the invention described above is used for desulfurizing an atmospheric distillate (GAS OIL) whose composition is given in Table 1:

TABLE 1

| LOADS | | GAS OIL | DSV 1 | DSV 2 |
|---|---|---|---|---|
| Gravity at 15° C. | | 0.8530 | 0.9221 | 0.9350 |
| Refractive index at 20° C. | | 1.4751 | 1.4970 | 1.5005 |
| Sulfur | % by weight | 1.49 | 2.13 | 3.13 |
| Total nitrogen | ppm | 108 | 880 | 1000 |
| Basic nitrogen | ppm | 26 | | |
| Viscosity at 20° C. | cSt | 7.03 | | |
| Viscosity at 50° C. | cSt | 3.49 | 41.50 | 76.13 |
| Viscosity at 100° C. | | | 7.96 | 11.67 |
| ASTM colour number | | 1.0– | | |
| Bromine number | Br$_2$ g/100 g | 2.30 | | |
| Conr. carb. | % by weight | | 0.27 | 0.31 |
| Flow point | °C. | –3.0 | 33.0 | 42 |
| Aniline point | | 71.1 | 83.1 | 83.4 |
| Molecular weight (method d-t50 D.86) | gr | 241 | | |
| Molecular weight (method d-visco 98.9° C.) | gr | | 390 | 422 |
| ASTM D3238 | | | | |
| Aromatic carbon | % at | 16 | 23 | 20 |
| Paraffinic carbon | % at | 63 | 64 | 62 |
| Naphthenic carbon | % at | 21 | 13 | 18 |
| Paraffins | % by weight | 40.10 | | |
| Non-condensed naphthenes | % by weight | 18.00 | | |
| Condensed naphthenes | % by weight | 11.10 | | |
| Aromatics | % by weight | 30.80 | 53.3 | |
| Distillation | | ASTM D.86 | ASTM D1160 | ASTM D1160 |
| Ip | % by vol./°C. | 219 | 323 | 299 |
| 5 | % by vol./°C. | 241 | 392 | 419 |
| 10 | % by vol./°C. | 255 | 400 | 430 |
| 30 | % by vol./°C. | 282 | 427 | 453 |
| 50 | % by vol./°C. | 302 | 448 | 476 |
| 70 | % by vol./°C. | 323 | 478 | 503 |
| 90 | % by vol./°C. | 352 | 527 | 536 |
| 95 | % by vol./°C. | 363 | 548 | 557 |
| EP | % by vol./°C. | 370 | 566 | 557 |

The distillate is a straight-run gas oil coming from a SAFANYIA crude, its sulfur concentration is 1.49% by weight. The reactor is filled with a hydrotreating catalyst (NiMo active phase on an alumina support) whose sulfurization is performed by means of a gas oil containing dimethyldisulfide. The load combined with hydrogen under pressure at a volume ratio of 400 liters of $H_2$ per liter of load is introduced. This hydrogen flow is measured at the plant outlet in order to always ensure the presence of hydrogen on the catalyst. The space velocity is adjusted by the flowmeter of the high-pressure pump. The performances obtained for two operating conditions are given in Table 2.

The pilot plant corresponds to the device according to the invention.

TABLE 2

GAS OIL HYDROTREATING

| | Pilot plant | | | Industrial plant | | |
|---|---|---|---|---|---|---|
| T (°C.) | Sulfur (S) ppm | HDS (%) | HDCA (%) | Sulfur (S) ppm | HDS (%) | HDCA (%) |
| 340 | 230 | 98.5 | 37 | 270 | 98.2 | 36 |
| 314 | 2640 | 82.3 | 18 | 2975 | 80.0 | 17 |

The experimental points are selected at two hydrodesulfurization performance levels. This range covers the current requirements for commercial diesel oil with 0.3% by weight sulfur content and the future demand for 0.05% by weight.

These sulfur cleaning rates (HDS) are obtained at two temperatures and compared with those obtained in high-capacity industrial plants (catalytic volume>2 liters) They are called industrial results.

The cleaning rates obtained according to the invention are similar to those obtained in an industrial plant. The sulfur concentration in the diesel oil cut (boiling points ranging from 150° C. to 380° C.) ranges from 0.023 to 0.2975% by weight. The slight differences observed for the sulfur concentration are within the analytical precision range and the operation precision range of a pilot plant.

The hydrogenation of the aromatics is quantified by the aromatic carbon decrease between the load and the effluent in relation to the aromatic carbon in the load. It is called HDCA This hydrogenation rate is also similar to that obtained in an industrial plant.

EXAMPLE 2

The invention is used to perform a hydrotreating test on vacuum distillates (DSV 1) whose petroleum characteristics are given in Table 1. The purpose of this test is to carry out the first stage of a vacuum distillate hydrocracking plant. In this case, a deep denitrogenation of the vacuum distillate DSV 1 is required in order to obtain a high purity in the total effluent coming out of the plant. The concentration is 800 ppm nitrogen in the DSV 1 used (see Table 1). The first stage conversion is also an important parameter.

TABLE 3

VACUUM DISTILLATE HYDROTREATING

| | Pilot plant | | | Industrial plant | | |
|---|---|---|---|---|---|---|
| T (°C.) | Nitrogen (N) ppm | HDN (%) | Conversion 380° C.-(%) | Nitrogen (N) ppm | HDN (%) | Conversion 380° C.-(%) |
| 370 | 3.2 | 99.6 | 27 | 2.5 | 99.7 | 26 |
| 394 | 0.2 | 99.97 | 64 | 0.3 | 99.97 | 65 |
| 410 | 11.0 | 98.8 | 37 | 8.0 | 99.1 | 35 |

In Table 3, the results show that the nitrogen cleaning rates (HDN) are similar to those of the industrial plant. The differences observed are within the nitrogen measurement and the plant operation analytical error range.

The conversions obtained are similar to those obtained with the industrial plant. It can be noted that, in the temperature range used (from 370° C. to 410° C.), no thermal cracking or cracking due to the walls is observed.

The cleaning rates measured confirm that the backmixing effects are negligible.

Figure 2:
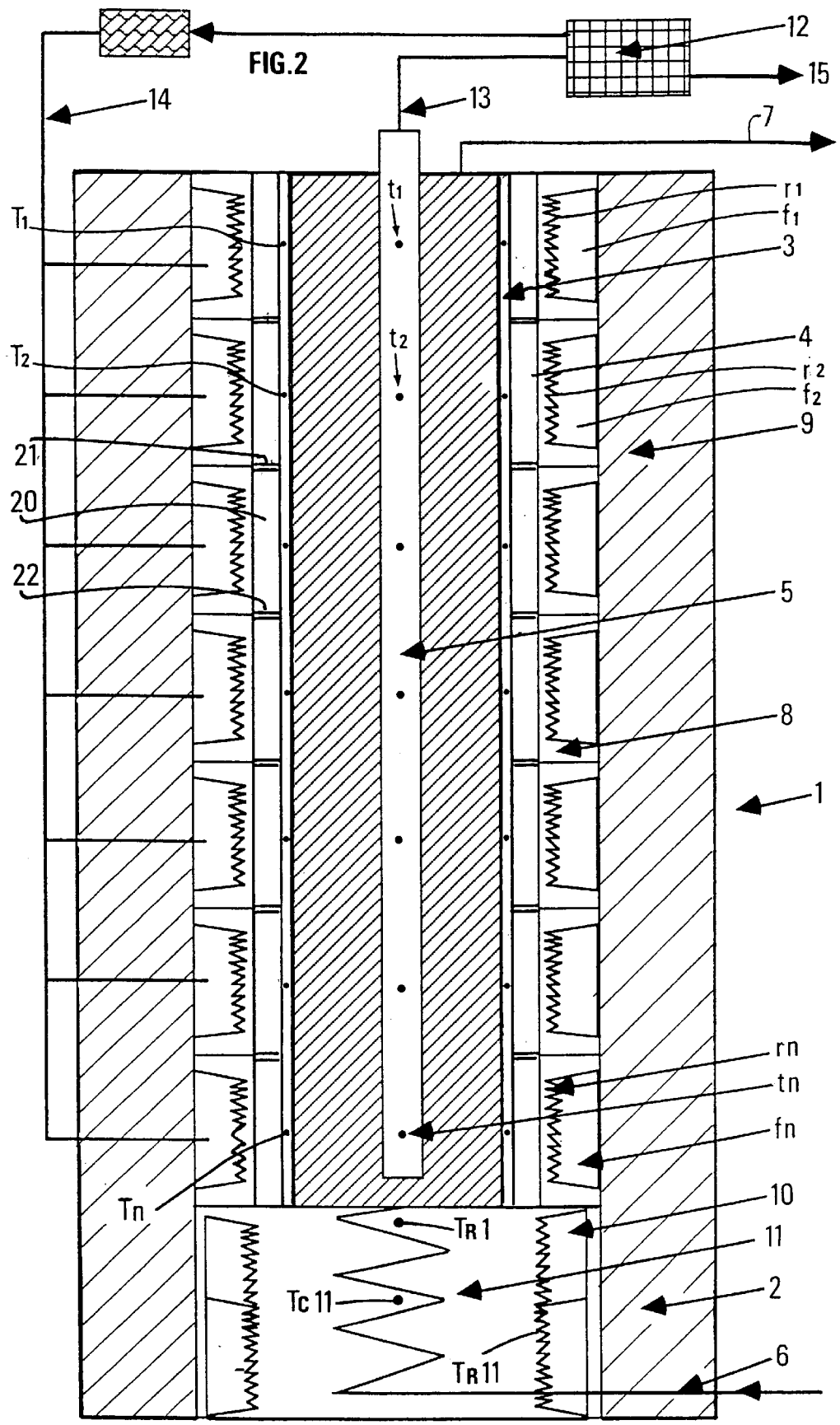
FIG. 2 shows a variant of the invention.

FIG. 2 shows a variant of the device according to the invention, in which the heating mode is achieved by radiation, at the level of the reactor or at the level of the preheat furnace.

In this case, coil 11 is a single-pass coil and it is surrounded by the electric resistor. The assembly consisting of the coil and the resistor is placed in an annular air space delimited by the casing of the preheat furnace that serves as a heat reflector. The coil and the resistor are no longer in contact. The heat is mainly transmitted by radiation. The end of the last spire of the coil in connection with the reactor is no longer compelled to pass through the axis of the preheat furnace and it forms directly the natural continuation of the spires. This improvement allows the distance between the furnace and the reactor, and therefore the heat losses to be reduced. The furnace is thus offset in relation to the reactor. Three skin temperature measurements are performed in different places of the coil, TR1 at the coil outlet, TC11 half-way up the coil and TR11 half-way on the skin of the heating resistor. The same temperature measurement configuration can be found for the conductive system described above (not shown in FIG. 1).

The means for heating the reactor consist of a series of electric resistors r1, r2, . . . , m inserted in metallic half rings surrounding the reactor. An annular air space 20 of the order of 3 cm separates the heating means from the external wall of reactor 3. The heat is transmitted by radiation. The whole of the reactor heating means consists for example of 7 (in this case, n=7) regulated heating zones, one of which (shell or ring fn) comprises the part corresponding to the coil-reactor junction. Shell fn (f7) is regulated to a set value corresponding to a skin temperature, of the reactor (Tn or T7). The other shells are regulated to a temperature internal to the reactor (thermocouples of sheathed thermometer 5:t1 to t6). The catalytic zone corresponds to shells f1 to f5. Each annular volume 20 around the reactor corresponding to a heating zone is limited by two insulating rings 21 and 22 that enclose the reactor. A stagnant air volume preventing in large part a chimney effect along the reactor thus corresponds to each heating zone (f1 to f7). In relation to the conductive system, the measuring point of the resisters skin temperature is preferably accessible.

The characteristics of the coil of the radiation preheat furnace can be as follows:
length: 4 meters minimum,
inside diameter: can range between 4 and 2 mm,
outside diameter: can range between 6 and 4 mm,
the coil is preferably sheathed with a copper tube.

In both variants, radiative or conductive, the enthalpy provided to the load preheat furnace is regulated by means of the set value imposed on the coil skin temperature, TC11, for limiting prohibitive temperature rises.

The following tests show the compared performances of the radiative heating system and of the conductive heating system.
1) Thermal cracking analysis at the level of the preheat furnace It may be reminded that the preheat furnace must bring the load as close as possible to the reaction temperature without causing any thermal precracking thereof.

The two systems, radiative and conductive, have been compared by processing a vacuum distillate DSV 2 whose composition is given in Table 1. The comparison has been established at different heat levels in the preheat furnaces, the reactor filled with glass marbles being maintained at a temperature of 150° C. The objective consisted in comparing the cracking level at the outlet of the furnaces. The cracking is quantified by follow-up of the simulated distillations of the liquid end products at the plant outlet. The passage through the reactor has no thermal effect.

All the experiments have been carried out with iso-residence times. The load combined with hydrogen under pressure with a volume ratio of 800 liters of $H_2$ per liter of load is introduced. The temperature of the preheat furnace corresponds to the coil skin temperature TC11, the set temperature of the regulator. The most important comparative results are collected in Table 4. The conversions given correspond to the net conversions into compounds whose boiling point is below 375° C. (375° C.- fraction) in the liquid end product.

$$375° \text{ C.-net conversion} = \frac{375° \text{ C.} + \text{load} - 375° \text{ C.} + \text{liquid end product}}{375° \text{ C.} + \text{load}}$$

TABLE 4

THERMAL CRACKING OF DSV 2 IN THE PREHEAT FURNACES

| Heating means | Furnace temperature TC11 (°C.) | Furnace outlet temperature TR1 (°C.) | Liquid end product R.I. | Liquid end product D15 | Net conversion 375° C.- |
|---|---|---|---|---|---|
| Conductive | 400 | 297 | 1.5009 | 0.9320 | 0.8 |
| Conductive | 420 | 316 | 1.5004 | 0.9299 | 3.2 |
| Radiative | 420 | 326 | 1.5014 | 0.9333 | 0.5 |
| Radiative | 420 | 315 | 1.5011 | 0.9323 | 0.7 |
| Radiative | 420 | 328 | 1.5013 | 0.9323 | 0.9 |
| Radiative | 430 | 336 | 1.5013 | 0.9308 | 1.3 |
| Radiative | 440 | 344 | 1.5011 | 0.9298 | 2.6 |

R.I.: refractive index (70° C.).

It seems that the radiative preheat furnace can be operated at a higher temperature TC11 (process tube skin) than the conductive system for the same cracking level ($\Delta t=20°$ C.). If one compares the two maximum temperature measurements observed on the two systems, TR11 (resistor skin) for the conductive system and TC11 (process tube skin) for the radiative system, this difference is only 5° to 10° C. in favour of the radiative system.

2) Thermal cracking analysis at the level of the reactor

The radiative and the conductive system having the same number and the same distribution of heating zones, one has tried to obtain the same thermal profile with the two systems.

The thermal cracking level observed at the level of the reactor with the conductive system has been compared with that obtained with the radiative system, with an iso-residence time, in the reactor, for the vacuum distillate DSV 2. In both cases, the preheat furnace is the same (radiative system) and it is maintained at a temperature for which it has been previously checked that the cracking is negligible. The reactor is filled with glass marbles (ø=2 mm). Table 5 gives the most important elements of this comparison.

TABLE 5

THERMAL CRACKING OF DSV 2 IN THE REACTOR FILLED WITH GLASS MARBLES

| Reactor heating means | Reactor temperature (°C.) | liquid end product R.I. | Liquid end product D15 | 375° C. net conversion |
|---|---|---|---|---|
| Conductive | 410 | 1.5003 | 0.9299 | 3.7 |
| Radiative | 410 | 1.5005 | 0.9298 | 3.4 |

R.I.: refractive index (70° C.).

The cracking quantified by the net conversion into compounds boiling below 375° C. (375° C.- fraction) is equivalent in both systems.

3) Comparison of the radiative and of the conductive system in catalytic tests

The pilot plant equipped successively with conductive heating means, then with radiative heating means such as described above, has been used to carry out hydrotreating tests on the vacuum distillate DSV 1 whose characteristics are given in Table 1.

In both tests, the reactor is filled with a hydrotreating catalyst (NiMo active phase on an alumina support) whose sulfurization is performed by means of a gas oil containing dimethylsulfide. The load (DSV 1) combined with hydrogen under pressure with a volume ratio of 800 liters of $H_2$ per liter of load is introduced.

The performances obtained for two operating conditions are given in Table 6.

TABLE 6

VACUUM DISTILLATE HYDROTREATING

| | Plant with conductive heating means | | | Plant with radiative heating means | | |
|---|---|---|---|---|---|---|
| T °C. | Nitrogen (N) ppm | HDN (%) | 375° C.- conversion % | Nitrogen (N) ppm | HDN (%) | 375° C.- conversion % |
| 370 | 245 | 72.16 | 12.4 | 240 | 72.72 | 12.1 |
| 390 | 42 | 95.23 | 21.2 | 48 | 94.54 | 21.7 |

The results show that the nitrogen cleaning rates (HDN) in the plant equipped with radiative heating means are similar to those obtained in the plant equipped with conductive heating means. The differences observed are within the nitrogen measurement and plant operation analytical error margin.

The conversions into compounds of boiling point below 375° C. (375° C.-) are also very close.

A priori, radiation heating must allow to reduce the thermal cracking in a small-size pilot plant whose type is described here. In particular, this type of caloric supply seems favourable at the level of the preheat furnace for thermally fragile loads (vacuum distillates, residues, . . . ).

We claim:

1. A device for testing and for analyzing a chemical reaction employing a load placed in contact with at least one catalyst, said device comprising at least one reactor for containing at least one catalyst, said reactor being of cylindrical shape having an outside diameter, a length L and an inside diameter D, means for heating said reactor to a temperature, means for controlling the temperature of said reactor, means for preheating a load prior to entry thereof in the reactor, thermal insulation means disposed at least exteriorly of the outside diameter of said reactor, wherein the inside diameter D ranges between 10 and 40 mm, said reactor has an L/D ratio of 50<L/D<150, said temperature control means comprises at least one sheathed thermometer arranged substantially along the axis of the reactor, and said reactor, arranged substantially vertically, comprises receiving means for the load through a lower or upper end of said reactor.

2. A device as claimed in claim 1, wherein the preheating means comprise a coil-shaped load delivery line and means for heating said coil-shaped load delivery line.

3. A device as claimed in claim 2, wherein said thermal insulation means also surrounds said coil-shaped load delivery line.

4. A device as claimed in claim 2, wherein said coil-shaped load delivery line is a double-wall tube having an inner and outer wall, the outer wall being made of a metal exhibiting a higher heat conductivity than the inner wall.

5. A device as claimed in claim 1, wherein said sheathed thermometer has a diameter ranging between 3 and 6 mm and comprises thermocouples distributed lengthwise thereof.

6. A device as claimed in claim 1, wherein L/D ranges between 70 and 100.

7. A device as claimed in claim 1, wherein said reactor has a diameter D of about 16 mm and a length L of about 1500 mm.

8. A device as claimed in claim 2, wherein the thermal insulation means comprises a cylindrical jacket made of two half shells placed around both the means for heating the reactor and the means for preheating the load delivery line.

9. A device as claimed in claim 1, wherein said reactor heating means comprises a series of electric resistors embedded in metallic half rings surrounding the reactor, said half rings being welded to each other so as to form two half shells around the reactor, two oppositely opposed half rings forming a ring, said ring comprising at least one means for measuring temperature of said ring, and thermocouples disposed lengthwise along the sheathed thermometer and proximate at least one transverse plane comprising said means for measuring the temperature of each ring.

10. A device as claimed in claim 9, wherein the temperature control means comprise means for regulating an electric supply of said each ring according to the temperature measured by the thermocouples of the sheathed thermometer and optionally by the means for measuring the temperature of each ring.

11. A device as claimed in claim 2, wherein the preheating means comprise electric resistors disposed in a heat-conducting material in contact with the load delivery line, so as to achieve conductive heating.

12. A device as claimed in claim 9, wherein said reactor heating means comprises an air layer between electric resistors of said each ring and the outside diameter of the reactor and, so as to achieve a radiative heating system.

13. A device as claimed in claim 12, further comprising annular insulating rings 21, 22 made of a thermally insulating material disposed between the reactor and said insulating rings so as to form sealed annular compartments of air.

14. A device according to claim 4, wherein the outer wall is made of copper.

15. A device according to claim 1, further comprising a coil-shaped load delivery line having an outside diameter for delivering the load into the reactor, wherein said preheating means comprises an electric resistor heater arranged to provide an air layer between said electric resistor heater and the outside diameter of said coil-shaped load delivery line so as to achieve a radiative heating system for said delivery line.

16. A device according to claim 1, said reactor containing said at least one catalyst.

* * * * *